(12) United States Patent
Feiler

(10) Patent No.: US 6,413,280 B1
(45) Date of Patent: Jul. 2, 2002

(54) HIP JOINT PROSTHESIS

(76) Inventor: Frederic C. Feiler, 10 Mesa La., Colorado Springs, CO (US) 80906

( * ) Notice: Subject to any disclaimer, the term of this patent is extended or adjusted under 35 U.S.C. 154(b) by 543 days.

(21) Appl. No.: 08/726,088

(22) Filed: Oct. 4, 1996

(51) Int. Cl.7 .............................. A61F 2/36; A61F 2/34
(52) U.S. Cl. ................. 623/22.15; 623/22.21; 623/23.35
(58) Field of Search .............. 623/22, 23, 19

(56) References Cited

U.S. PATENT DOCUMENTS

| | | | | | |
|---|---|---|---|---|---|
| 3,848,272 | A | * | 11/1974 | Noiles | 623/23 |
| 4,279,041 | A | * | 7/1981 | Buchholz | 623/23 |
| 4,978,356 | A | * | 12/1990 | Noiles | 623/18 |
| 5,092,897 | A | * | 3/1992 | Forte | 623/22 |
| 5,507,819 | A | * | 4/1996 | Wolf | 623/19 |

FOREIGN PATENT DOCUMENTS

| | | | | |
|---|---|---|---|---|
| DE | 3600804 C1 | * | 8/1987 | 623/23 |
| EP | 0 359 672 A1 | * | 3/1990 | 623/23 |
| EP | 0 363 019 A3 | * | 4/1990 | 623/23 |
| EP | 0 552 949 A1 | * | 7/1993 | 623/22 |
| SU | 1724208 | * | 4/1992 | 623/22 |

* cited by examiner

*Primary Examiner*—David H. Willse
(74) *Attorney, Agent, or Firm*—Richard W. Hanes; Hanes & Schutz, P.C.

(57) ABSTRACT

A hip joint prosthesis comprising a femoral stem, adapted for implant into the medullary canal of a human leg femur, said stem having a superior neck portion whose longitudinal axis is arcuate, forming concave and convex portions thereof, and terminating in a globular femoral head, and an acetabular cup, adapted to be attached to a human pelvis. The cup is sized and shaped to rotatingly receive the femoral head. The inferior portion of the cup is relieved by an indentation therein which accommodates the convex contour of the arcuate neck during extension and abduction of the leg. The concave portion of the neck is adapted to arch over and avoid interfering with the superior rim of the cup during hyperflexion of the leg. The indentation in the inferior portion of the cup is intended to receive and accommodate the convex contour of the arcuate neck during extension and abduction of the leg.

3 Claims, 3 Drawing Sheets

HIP JOINT PROSTHESIS

The present invention relates to an implantable prosthesis adapted to be inserted into a human body. More particularly, the invention relates to a prosthesis adapted to replace the junction between a pelvis and femur, i.e. a hip joint, including both the femoral portion and the acetabular cup.

BACKGROUND OF THE INVENTION

Hip joint prostheses comprising a femoral stem and a cooperating acetabular cup have been in use for many years. The success rate of such implants continues to grow with increasing implant experience and the advent of new prosthesis materials, however one problem remains extant that has not abated with maturity of the procedure. The residual problem is that of the patient dislocating the hip prosthesis as a result of flexion, adduction and internal rotation of the hip joint which exceeds the ability of the components of the apparatus to remain in their intended relationship, that is for the ball, or head, to remain within the confines of the socket, or acetabular cup.

It is therefore the primary object of the present invention to provide a hip prosthesis which will accommodate substantially greater degrees of flexion, adduction and internal rotation than prior art prostheses without dislocating, that is, without the femoral head being dislodged from the cavity of the acetabular cup.

Another object of the invention is to remedy the dislocation tendency of prior hip prosthesis, and at the same time provide the patient the freedom to squat or abduct the prosthetic leg, that is, to provide for greater leg flexion, abduction and internal rotation than similar prostheses of the prior art, while at the same time allowing normal extension and abduction of the hip joint.

DETAILED DESCRIPTION

Figure 7:
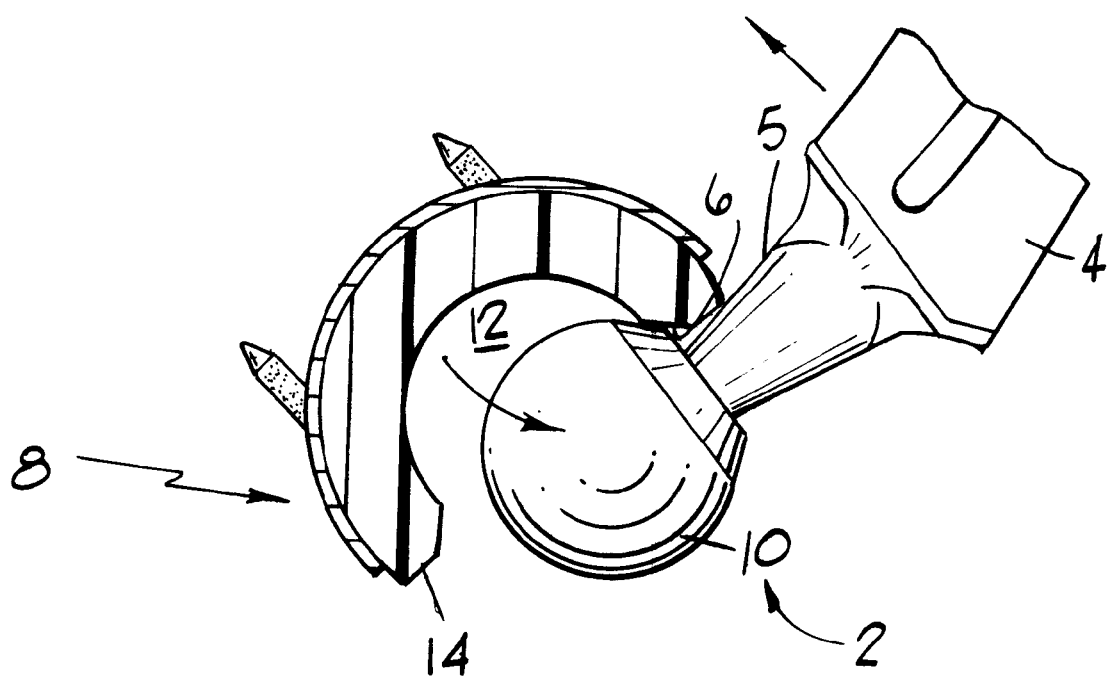
FIG. 7 is a side view of a typical hip joint prosthesis of the prior art, with the acetabular cup shown in cross section, and showing a femoral head dislocating from the cavity of the acetabular cup.

As an introduction to the present invention, refer to FIG. 7 where a prior art prosthesis 2 is shown in the process of dislocation. It is seen that when the leg (not shown in the drawings) in which is implanted the femoral stem 4 is hyperflexed, the straight neck portion 5 of the femoral stem component comes into contact with the superior rim 6 of the acetabular cup 8, forming the fulcrum of a first class lever, where the elongated femoral stem 4 and the integrated leg act as the power bar. Accordingly, further flexion of the leg, and consequent movement of the stem and neck, results in prying the head 10 out of the confines of the cup cavity 12. Once the head 10, or ball, is raised up and out of its normal position within the acetabular cup 8 the leg muscles tend to further dislocate the components by pulling the head 10 past the opposing cup rim 14 into a position of full dislocation.

Figure 1:
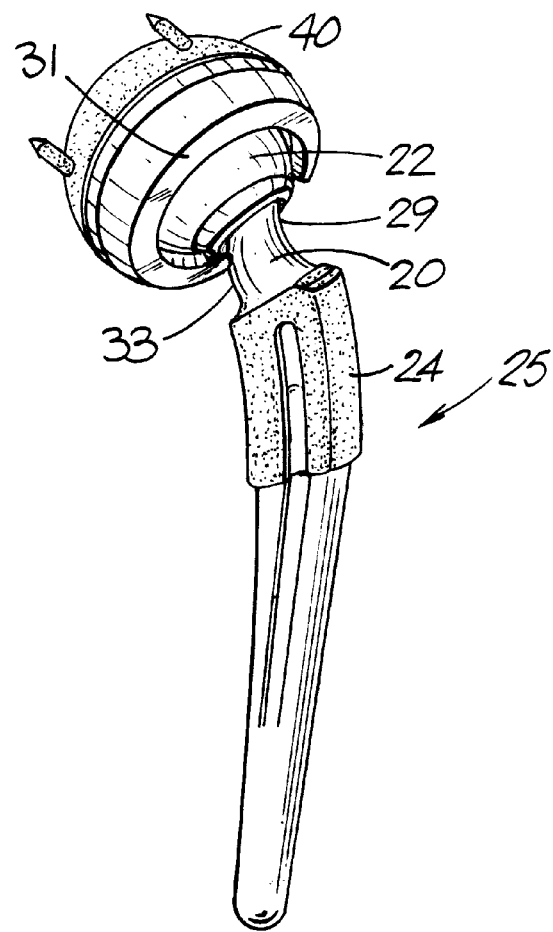
FIG. 1 is a perspective view of a left hip prosthesis of the present invention, showing the head of the femoral stem disposed within the cavity of the acetabular cup and the femoral stem being in the position it would assume during normal extension of the leg.
Figure 2:
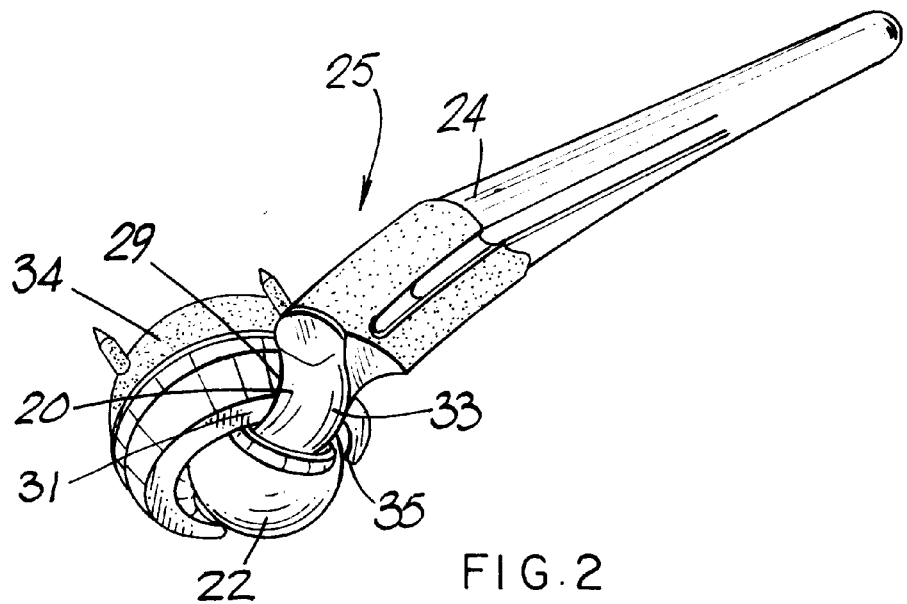
FIG. 2 is a perspective view of the prosthesis of the present invention with the femoral stem being in the position it would assume during hyperflexion of the leg.
Figure 3:
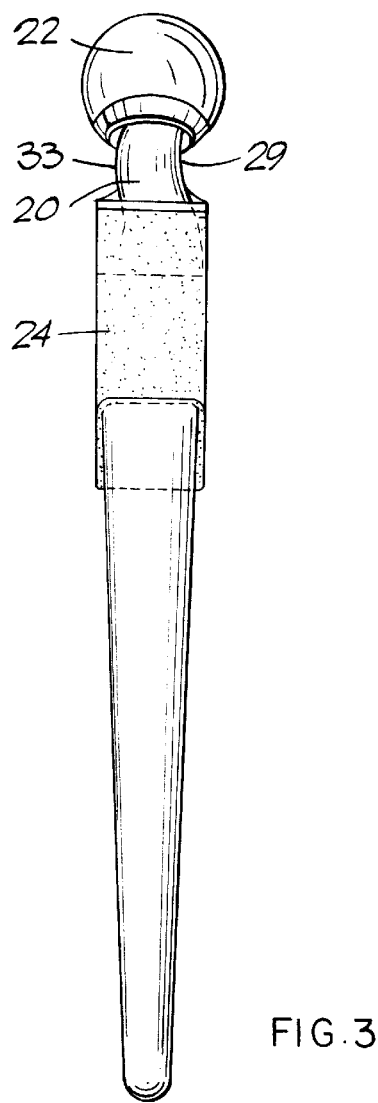
FIG. 3 is an end, or lateral, view of the femoral stem of the prosthesis of the present invention. When implanted in a human leg, the left side of the device, as seen in this FIG. 3, would be the posterior side, which the right hand side would be the anterior side.
Figure 4:
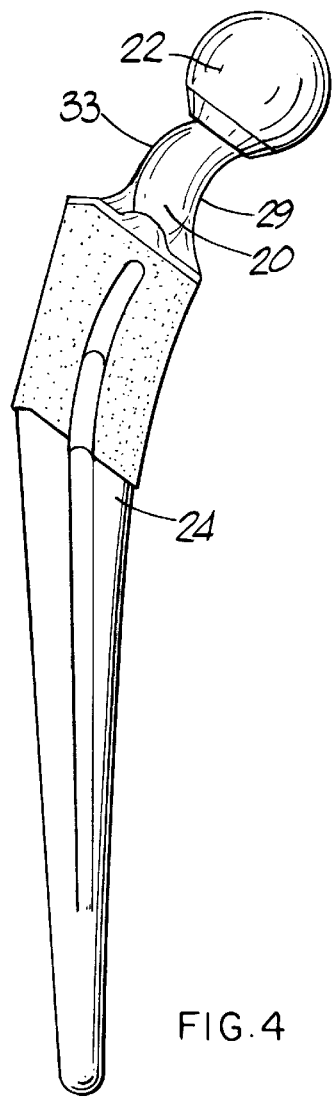
FIG. 4 is a view of the anterior side of the femoral stem of the prosthesis of the present invention.
Figure 5:
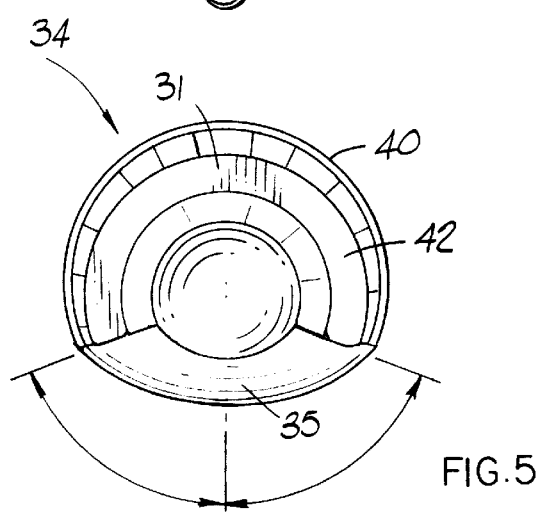
FIG. 5 is a top view of the acetabular cup of the present invention.
Figure 6:
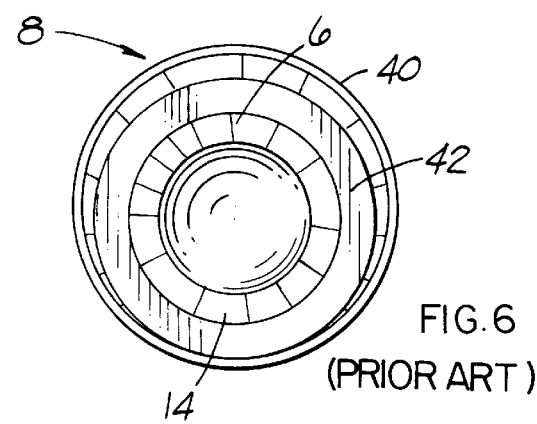
FIG. 6 is a top view of an acetabular cup of the prior art.

In the prosthesis of the present invention the neck 20, which interconnects the head 22 and the stem 24 of the prosthesis 25, is bowed, or curved. Because of the angle at which the femoral stem is disposed when implanted in the femur of the leg (approximately 10° from the frontal plane), it is preferable, in order to accomplish the objects of the invention, to establish the curve of the neck in two planes. The curvature of the neck 20 is made in what would be equivalent to both the sagittal and frontal planes of the implanted device, as shown in FIGS. 3 and 4. In both the front and side views of the femoral component, the bowed neck 20 is seen as having a concave curvature 29 on that side of the neck which would tend to contact the superior cup rim 31 during hyperflexion of the leg. The degree of curve, or concavity, or the particular form or contour thereof is a matter of design choice so long as the required spatial relationship between the head 22 and the femoral stem 24 is maintained. The concavity of the neck 20 permits a significant number of additional degrees of hyperflexion over the prior art design of a straight neck portion 5 (See FIG. 7, the prior art). The attainment of additional degrees of stem and head rotation is possible because the concave portion of the neck arches over the superior cup rim, providing the opportunity for greater angular movement, or hyperflexion of the leg.

Creating a significant enough concavity in the neck to accomplish the object of permitting greater hyperflexion, would however, weaken the neck 20 unless a corresponding adjustment in the shape of the neck were made. Such a reconciliation is made by maintaining the cross sectional area of the neck while making convex that side 33 of the neck 20 which is opposite to the concave side 29. Creating what appears to be a knuckle or elbow 33 to form the convex side of the neck, however, creates a problem of interference between the elbow portion 33 of the neck and the inferior rim of the acetabular cup when the leg is extended. In fact, unless accommodation is made for the elbow 33, normal extension of the leg would probably not be possible because of this interference. Accordingly, the prosthesis of the present invention solves this potential problem by relieving the inferior portion of the acetabular cup 34 to such an extent that, during normal leg extension, the elbow portion 33 of the neck 20 will be received in a notch 35 which is cut out of the inferior portion of the acetabular cup. The width of the notch 35 should be of such extent as to also accommodate the neck's elbow 33 when the leg is abducted. The presence of the notch 35 in the inferior portion of the cup will not diminish the structural integrity of the prosthesis or its ability to support the body weight of the patient because the weight bearing forces are concentrated between the femoral head and the superior portions of the acetabular cup. Here again, the exact shape and configuration of the notch 35 is a matter of design choice.

It is to be understood that an acetabular cup usually comprises a metallic base member 40 which is inserted into the pelvis in one of several ways, that is for example, by the use of parallel or diverging pegs which protrude from the base member, by screws, by an interference fit, or by cement The base member 40 is traditionally contains a liner 42 made of an ultra high molecular weight polyethylene (UHMWP), ceramic or some other material. In this specification, and in the included claims, the term "acetabular cup" shall be taken to mean a cup with or without a lining. Reference in this specification and the claims to posterior, anterior, superior, etc. or to the various planes associated with a human body, i.e. sagittal, frontal etc., are intended to relate to the devices of the present invention as they would appear in their normally implanted position in the human body.

I claim:

1. A hip joint prosthesis comprising, a femoral stem, adapted for implant into the medullary canal of a human femur, said stem having a superior neck whose longitudinal axis is arcuate, forming concave and convex contours, and terminating in a rounded femoral head;

an acetabular cup adapted to be attached to a human pelvis, sized and shaped to receive the femoral head for rotating movement therein, wherein an inferior portion of the cup is indented to accommodate the convex contour of the arcuate neck during extension and adduction of the femur;

wherein the longitudinal axis of the neck is curved anteriorly of a substantially frontal plane of the stem and laterally of a substantially sagittal plane of the stem.

2. A hip joint prosthesis comprising, a femoral stem, adapted for implant into the medullary canal of a human femur, said stem having a superior neck whose longitudinal axis is curved anteriorly of a plane which is substantially frontal with respect to the implanted stem and laterally of a plane which is substantially sagittal with respect to the implanted femoral stem, forming a neck elbow and a corresponding neck concavity, terminating in a rounded femoral head.

3. The prosthesis of claim 2 and further comprising an acetabular cup adapted to be attached to the human pelvis, having a concave body sized and shaped to receive the femoral head and bounded by a circumferential rim having a superior portion and an inferior portion, wherein the inferior portion contains an indentation that extends into the body of the cup to accommodate the outside neck elbow of the stem during extension and adduction of the femur.

* * * * *

UNITED STATES PATENT AND TRADEMARK OFFICE
CERTIFICATE OF CORRECTION

PATENT NO.    : 6,413,280 B1
DATED         : July 2, 2002
INVENTOR(S)   : Frederic C. Feiler It is certified that error appears in the above-identified patent and that said Letters Patent is hereby corrected as shown below:

<u>Column 1,</u>
Line 18, delete "adduction and internal" and add -- abduction and external --;
Line 25, delete "adduction and internal" and add -- abduction and external --;
Line 33, delete "internal" and add -- external --.

Signed and Sealed this

Nineteenth Day of November, 2002

*Attest:*

*Attesting Officer*

JAMES E. ROGAN
*Director of the United States Patent and Trademark Office*